United States Patent [19]
Shepherd

[11] Patent Number: 5,227,059
[45] Date of Patent: Jul. 13, 1993

[54] CHROMATOGRAPHY COLUMNS

[75] Inventor: Peter Shepherd, Cheshire, United Kingdom

[73] Assignee: Alltech Associates, Inc., Deerfield, Ill.

[21] Appl. No.: 610,399

[22] Filed: Nov. 7, 1990

[30] Foreign Application Priority Data

Nov. 8, 1989 [GB] United Kingdom ............... 8925225.8
Jul. 28, 1990 [GB] United Kingdom ............... 9016620.8

[51] Int. Cl.$^5$ .............................................. B01D 15/08
[52] U.S. Cl. .................... 210/198.2; 55/386; 73/61.53
[58] Field of Search ...................... 210/198.2, 656, 232; 55/386; 285/12; 73/61.1 C, 61.52, 61.53

[56] References Cited

U.S. PATENT DOCUMENTS

| | | | |
|---|---|---|---|
| Re. 31,974 | 8/1985 | Brownlee | 55/386 |
| 3,440,864 | 4/1969 | Blume | 73/61.1 |
| 3,474,908 | 10/1969 | Catravas | 210/198 |
| 3,487,938 | 1/1970 | Patterson | 210/198 |
| 4,313,828 | 2/1982 | Brownlee | 55/386 |
| 4,451,363 | 5/1984 | Brownlee et al. | 55/386 |
| 4,522,715 | 6/1985 | Walters et al. | 210/198.2 |
| 4,670,141 | 6/1987 | Shackelford et al. | 210/656 |
| 4,732,687 | 3/1988 | Müller et al. | 210/198.2 |
| 4,962,042 | 10/1990 | Morabito et al. | 55/386 |

FOREIGN PATENT DOCUMENTS 40663  5/1980  European Pat. Off.

Primary Examiner—Mary Lynn Theisen
Assistant Examiner—Sun Uk Kim
Attorney, Agent, or Firm—Donald W. Margolis

[57] ABSTRACT

The present invention relates to chromatography, and provides in a chromatography column new end fittings and an insert. Each end fitting is a plastics plug which is screwed to the end of the column tube, and inside the end fitting is a shoulder which is engaged by an insert. The insert fits neatly into the column tube so that it can be used to press against the column packing. The insert also embodies a cavity for a frit, and the end of the insert which projects into the column and seats against the column packing, has a skirt which is flared so that the pressure inside the column will spread the skirt which is of flexible plastics material into sealing contact with the column inner wall forming an effective seal. The insert may be in one piece plastics material component, or it may be in two pieces, a plastic piece embodying the skirt and stainless steel piece has the portion which engages the shoulder.

23 Claims, 4 Drawing Sheets

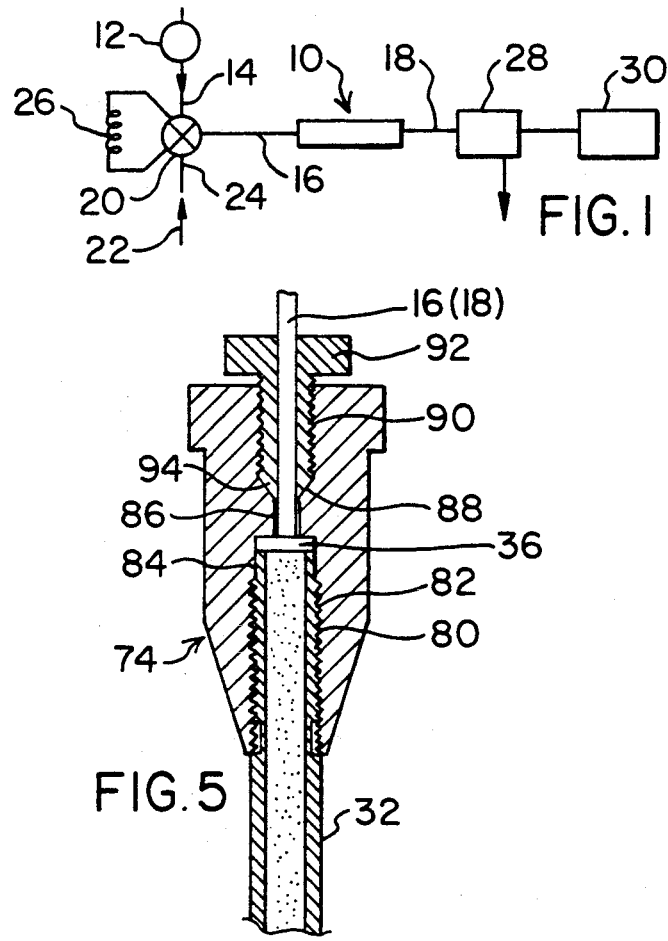
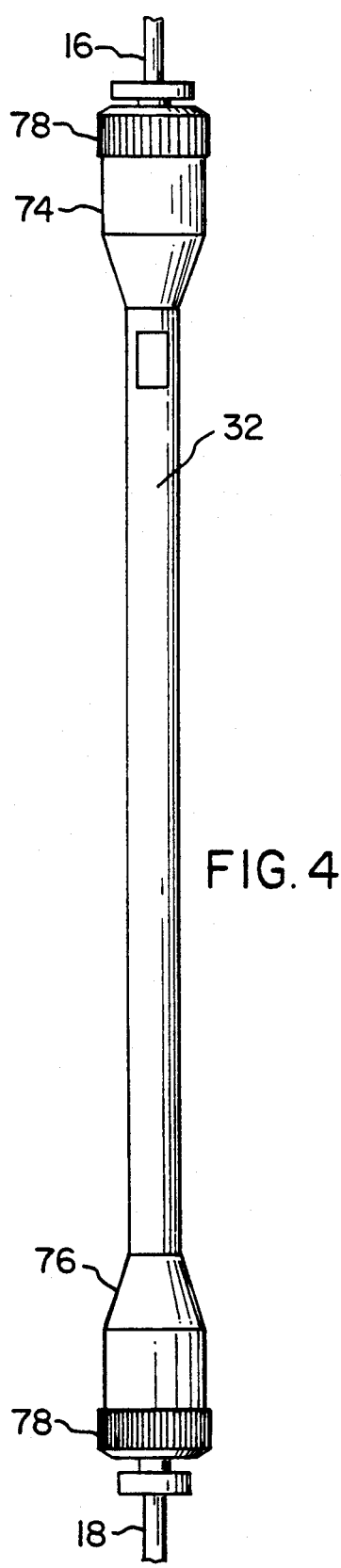
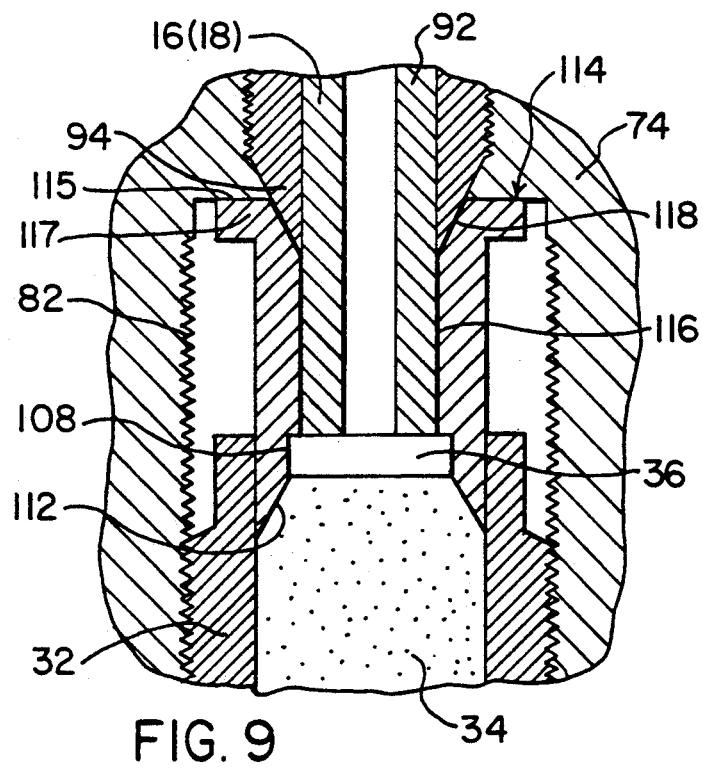

CHROMATOGRAPHY COLUMNS

This invention relates to chromatography columns both in their construction and in their embodiment in chromatography systems.

Chromatography provides a means whereby the components, phases, ingredients, substances, in a fluent mixture or material may be progressively adsorbed in that the fluent material is forced under pressure through a tube which contains an adsorbent medium, which is tightly packed particulate material. The packing material is selected for its adsorbing characteristics, and as the fluent material is forced through the column, so its constituents are progressively adsorbed in time and/or in position relative to the column. A detector coupled to the outlet of the chromatography column serves to detect and display by means of graphical representation known as an elution curve, the various constituents of the mixture and the relative concentrations in the mixture. The elution curve is a series of spaced sharp peaks, and the sharper and more defined the peak, the better the functional operation of the chromatography column.

In order to protect the packing material which in many cases may be quite expensive, it is usual to top and tail the column tube with filters in the form of sintered metal discs, and these are held in positions by fittings which fit to the end of the column tube, said fittings also providing a means whereby the column can be connected to pipe work through which the material to be analysed is forced under pressure.

Chromatography columns come in a range of sizes, and depending upon size so they are utilised for different purposes. For example, the smaller chromatography columns, having tubes with internal diameter in the order of 6.5 mm, are mainly used for analytical work in order to analyse sample constituents. The intermediate size of chromatography column may be used for semi-preparatory work in which a material is passed through the column with a view not only to identifying its constituents, but also the amount of each constituent in the sample so that a larger batch of the material can be passed through even larger sized chromatography columns for isolation of particular substances for the production of same.

In chromatography columns at the small end of the scale, high hydraulic pressures are used for forcing the material through the column, and the hydraulic pressures needed for this may be in the order of 6000 psi. With such pressures it is important that the end fittings connecting the pipe work to the column, are of a high seal quality so that leakage will not occur. Also in the region of the end fitting, it is important to provide that there is minimum disturbance of the flow of the sample into the column tube, and also that voids or dead spaces in the column might be avoided, because a column which has or develops such voids or dead spaces tends to give rather poor readings reflected in shoulders in the peaks of the elution curve, or peaks which are indistinct.

Columns may develop voids as a result of passage of the fluent material to be tested through the packing, or they may develop as a result of flushing the column with solution, a procedure which takes place after a sample has been passed through the column, in order to regenerate the column for further use. Additionally, voids can be created during the packing of the column and appear as spaces at the ends of the column as the packing material settles in use.

Typically, the hydraulic connections referred to above are made conventionally using ferrule seals insofar as the ferrules are wedged against the pipe work connecting the column in a chromatography system and also connecting the fittings to the column tube resulting from relative screwing of the fitting components to wedge the ferrule, which is typically conical in shape, against a ferrule seat surface in the fitting and eventually onto the pipe work or column tube.

The present invention seeks to provide novel end fitting arrangements, in order to enhance the construction appearance and operation of chromatography columns.

In a first object of the invention, an end fitting is provided with an insert for reducing or eliminating voids or dead spaces in the column packing.

A further object of the invention is to provide an insert of relatively simple construction and effective design A further object of the invention is to provide an end fitting cap of a design enabling simple and effective coupling of the end cap to the system pipe work and the column tube.

A further object is to provide that in an insert end fitting, appropriate accommodation is made for receipt of an insert.

In a further object of the invention, the insert and fitting cap co-operate in their application to the column tube to provide for void or dead space elimination.

A still further object of the invention is to provide an end fitting system in plastics material whereby chromatography columns can be produced of an enhanced appearance and in less expensive construction.

In a still further object of the invention, the end fitting system has an adaptor for holding a guard column.

These and other objects of the invention are met at least by the preferred embodiments of the invention in the various aspects thereof which are described hereinafter In accordance with the first aspect of the invention there is provided in or for a chromatography column comprising a column tube for holding the packing medium and having adjustable end fittings connected thereto;
an insert embodied in or for embodiment in at least one of said end fittings, said insert comprising
a) a body portion which extends into or is adapted to extend into the adjacent end of the column tube,
b) a passage through said body portion to enable the passage through the insert of the fluent material to be passed through the column; and
c) a thrust face means connected to the body portion thrust engaging or for thrust engagement with said fitting,
whereby adjustment of the end fitting effects adjustment of the extent to which the insert projects into the column tube to reduce or eliminate voids in the column packing medium.

According to a further aspect of the invention there is provided a chromatography column comprising a column tube for holding the packing medium and having adjustable end fittings connected thereto and including;
an insert embodied in at least one of said end fittings, said insert comprising;
a) a body portion which extends into the adjacent end of the column tube and presses against the packing medium, and sealingly engages the inner surface of the column tube; and b) a passage through said body portion to enable the passage through the insert of the fluent material to be passed through the column;

said end fitting being adjustable to adjust the extent to which the insert projects into the column tube to reduce or eliminate voids in the column packing medium.

The insert may be in a single piece of suitable material such as steel or plastics or it may be in two portions, one of plastics and the other of steel.

In yet a further aspect of the invention there is provided a chromatography column comprising a column tube for holding packing medium having ends and having end fittings connected thereto, and at least one of said ends of the column tube the tube is threaded and the fitting is screwed thereto, and wherein said end fitting comprises a cap having a first end and a second end, and a passage therethrough extending between the first and second ends, said passage comprising in a direction from the first end to the second end, a threaded portion by which the cap is screwed to the column tube end, a narrow neck portion, a ferrule seat portion and a further threaded portion for receiving a ferrule clamping screw.

Embodiments of the present invention, and various aspects and features therof, will now be described, by way of example, with reference to the accompanying drawings, wherein;

FIG. 1 is a diagramatic view of a high pressure liquid chromatography (HPLC) system;

FIG. 4 is a side elevation of a chromatography column according to one embodiment of the invention;

FIG. 5 is an enlarged sectional elevation of one of the ends of the column shown in FIG. 4;

FIG. 9 is a view similar to FIG. 8, but showing a modified arrangement for the insert shown in FIG. 8;

Figure 2:
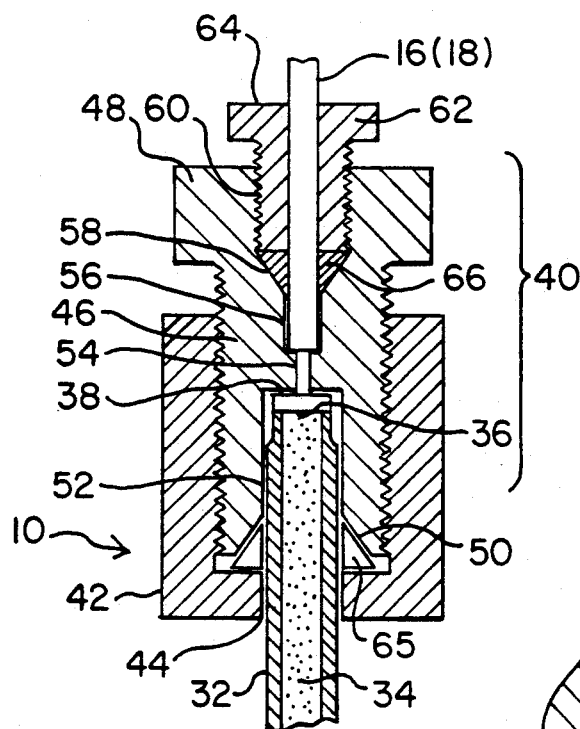
FIG. 2 is an enlarged sectional view of one end of a conventional chromatography column such as might be included in the system of FIG. 1.

High Pressure Liquid Chromatography is used for the separation of substances in a mixture or solution by adsorption as the mixture flows over an adsorbent medium, usually in a column, each substance finally being washed off the column at a different level or band that is recoverable, for example as by being washed off as pure solvent. A chromatography column can be used for analysis, or semi-preparatory work, and for substance production, and as the column is designed for these respective purposes, it tends to increase with size. The description hereinafter is mainly directed to chromatography columns which are used for analysis and therefore they are at the smaller end of the size scale e.g. of the size in the order of 6.5 mm in diameter and of a length in the order of 525 cm. Considerable pressures are required to drive the mixture through the adsorbent medium, and such pressures may be in the order of 6000 psi. Because such high pressures are involved, it is necessary that the couplings of the respective pipework lengths must be secure and must be effectively sealed. Similar considerations apply to the larger columns used for semi- preparatory work and for production.

Referring now to FIG. 1, a system for HPLC is diagrammatically illustrated, and the chromatography column is indicated by reference numeral 10. Reference numeral 12 indicates a high pressure pump by which the fluent mixture can be forced through the column 10 via pipe work 14 16 and 18. 20 represents a control valve by which solvent may be forced through the pipe work 14, 16 and then through the column 10 and through pipe work 18, or by which a sample to be analysed supplied as indicated by arrow 22 may pass through pipe work 24, into and out of the valve 20 and through further pipe work 26 and then into and out through the valve 20 and eventually through pipe work 16 and the column 10. Operation of the valve 20 controls whether or not the sample is applied through pipe work 16 or solvent is applied through pipe work 16, to the column 10.

Reference 28 represents a detector which detects and analyses the resulting material passing from pipe work 18 into the detector, and reference 30 indicates an integrator by which the results detected by the detector 28 may be integrated to provide or display meaningful results, such as elution curves having peaks to represent the different substances in the sample.

The chromatography system described in relation to FIG. 1 is well known and widely used. Different configurations of the system may be adopted to suit different purposes, but such different purposes are not of particular concern in the instant invention, which is concerned with the construction of the chromatography column 10 itself.

In the use of a chromatography system for analysis, the pipe work 14, 16, 18 is in fact relatively small sized. For example, pipe work 14 may have an internal diameter of the order of 500 micron, whilst pipework 16 and 18 may have an internal diameter of the order of 118 micron. This pipe work must be connnected so as to enable the fluent materials, delivered at high pressure as referred to herein, to pass through the absorbent medium of the column and therefore the couplings between the pipe work 16 and 18 and the column 10 must be securely arranged in order to prevent leakage.

Figure 3:
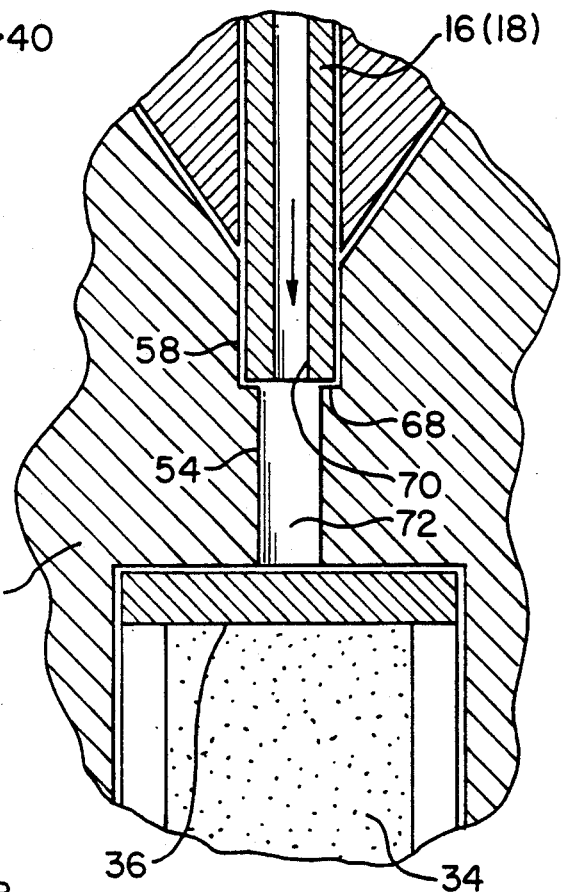
FIG. 3 is an enlarged sectional elevation of a detail shown in FIG. 2.

One form of conventional prior art coupling provided for each end of the column 10 is shown in FIGS. 2 and 3, and referring to these figures, the chromatography column 10 comprises a column tube 32 which is typically of stainless steel with smooth inner and outer surface characteristics. The tube 32 is packed tightly with the adsorbent medium 34 so that the medium lies flush with each end as indicated at 36 in FIGS. 2 and 3. On top of each end of the tube is provided a sintered metal disc 38 or the like, which is commonly known as a "frit", the sintered metal serving as a filter for the mixture which is forced through the adsorbent medium 34.

Each end of the tube 32 is provided with a fitting 40 which comprises an internally threaded cup member 42 having a central hole 44 in the base thereof and through which the tube 32 passes as shown, and a plug 46 which has a central passage therethrough and is externally threaded so as threadedly to engage the interior of the cup 42. The plug 46 has a hexagonal head 48 whereby it may be screwed into the cup 42 for the further connection of the plug to the cup.

The central passage through the plug comprises from the bottom up in FIG. 2, a frusto-conical portion 50, a cylindrical portion 52 leading from the frusto-conical portion and which receives the top end of the tube 32 and the frit 38, a small diameter injection bore 54, a larger diameter cylindrical bore 56 for receiving the end of the pipe work 16 or 18, a further frusto-conical portion 58, and finally top threaded portion 60 which receives a threaded plug 62 having a flange 64 by which the plug can be screwed into the threaded portion 60.

A locking ferrule 65 engages the frusto-conical portion 50 and sits on the base of the cup 42 so that as the cup and plug 42 and 46 are screwed together tightly, the frusto-conical ferrule 65 wedges against the bore 50 and therefor against the outer surface of the tube 32 whereby the fitting becomes locked on and sealed to the tube 32.

When the plug 64 is screwed into the cup 46, a further ferrule 66 engaging bore portion 58 is urged downwardly against said bore portion and in fact is wedged against the pipe work 16 or 18 in order to lock and seal the pipe work to the fitting 40.

A fitting of the nature described generally has it components fabricated in stainless steel, as is the pipe work 16 and 18, although some use of plastics material has been adopted for these components.

If reference is made to FIG. 3, it will be seen that the pipe work 16 or 18 enters the plug 46 to an extent to seat upon shoulder 68 between the bore section 58 and bore section 54, and the lower bore section 54 is smaller in diameter than bore section 58, but in fact because of the wall thickness of the pipe work 16 and 18, the size of the bore 70 of the pipe work 16 or 18 is smaller than the size of bore portion 54, and therefore when the mixture to pass through the column adsorbent medium 34 issues from the end of the pipe work 16 or 18, it enters a cavity 72 of larger diameter and therefore experiences an expansion and reduction in velocity. Although the sizes are very small, because chromatography measures in small amounts, this can have an effect on the resulting readings. It is desirable to make the size of bore 54 the same as bore 70, but because the sizes are so small, and it must be remembered that it is not practical to drill bore 54 to such small size, generally therfore prior art chromatography columns adopt ther arrangement as shown in FIG. 3 which tolerates the use of a bore section 54 which is larger than the bore size of the pipe work. The length of the bore 54 is sometimes referred to as the "Ferrule depth".

FIG. 4 shows a chromatography column according to one embodiment of the present invention. To facilitate understanding, numerals which have been used before in relation to FIGS. 2 and 3 will also be used in the following figures to designate the parts already described. The column shown in FIG. 4 is in fact a full sized illustration, and the column tube 32 is clearly shown, but it will be seen that the end fittings 74 and 76, which are identical, are of a different and improved configuration. Each end fitting is essentially a circular sectioned component and at the end remote from the adjacent column tube end is provided with a ring of knurling 78, whereby the fitting can be screwed to the top of the tube 32 as shown in FIG. 5. For large columns, this ring may be replaced by flats or a hexagonal section whereby turning of the end fitting, by a spanner or like tool, may be effected. It will be noted from FIG. 4 that the column has an improved slimline appearance.

Referring to FIG. 5 in more detail, it is to be noted that the top end of the column tube 32 is threaded as shown at 80, and the fitting cap 74 is internally threaded to mate with the threads 80. The fitting cap 74 is provided with an internal passage comprising a cylindrical threaded section 82 leading to a plain cylindrical section 84 of approximately the same size as the threaded section, followed by a narrow small diameter or neck section 86, followed by a frusto-conical section 88 and finally a further threaded section 90 which receives a plug 92 which is similar to the plug 62 except that it has a frusto-conical end 94 which replaces the ferrule 66 shown in FIG. 2, which makes it a ferrule clamp plug.

As shown clearly in FIG. 5, the pipe work 16 or 18 extends through the bore section 86 so as to lie flush with the top of the frit 36 and therefore the ferrule depth has been reduced to zero which gives enhanced performance of the column. The coupling of the fitting cap 74 to the tube 32 is simply by turning and tightening of the threads 80, 82 and the coupling of the pipe work 16,18 to the fitting cap 74 is by means of the plug 92 reacting against the frusto-conical portion 88 and deflecting the material of the plug in the region 94 into firm frictional and sealing engagement with the pipe work 16, 18.

In this connection, it is preferred that the plug 74 be fabricated or moulded or otherwise produced in suitable synthetic plastics material having the desired characteristics for this application. Additionally, it is preferred that the plug 92 be constructed of a like material. Furthermore pipework 16 and 18 may be of the appropriate plastics material, and indeed in the final analysis is preferred that tube 32 is formed of approprate plastics material.

Suitable materials for these components and all other components of other embodiments of the invention are (i) the plastics material sold by Du Pont under the trade mark DELRIN, which is a homopolymer; (ii) acetalcopolymer, and in particular a suitable material is a material known as "PEEK" sold by ICI, which is a Polyetheretherketone; the material KEL-F; and (iv) PTFE. The PEEK material is proving to be particuarly suitable for these components but any other suitable material may be used. Additionally, as regards the embodiments of the invention described hereinafter, it is envisaged that they may preferrably be constructed from suitable plastics material such as those indicated above. The plastics material preferably is chemically inert and has characteristics as close to steel as possible.

The fitting and coupling arrangement as shown in FIGS. 4 and 5 is particularly neat and efficient and furthermore eliminates the "ferrule depth".

Figure 6:
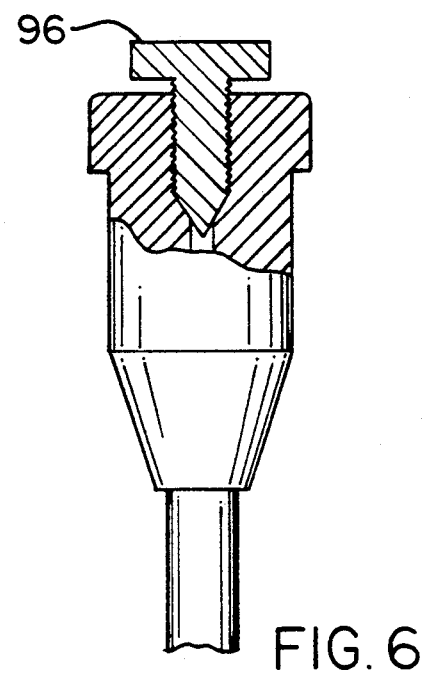
FIG. 6 is an enlarged part sectional elevation similar to FIG. 5 which shows the utilisation of a blank plug for use when the column is being stored or transported.

In chromatography, it is of course necessary to fill or pack the column or more particularly the column tube 32, with the adsorbent medium. There is a well known technique, and the method is to couple one end of the column to a supply source of the medium which typically will comprise the medium and the solvent for other carrier solution, as the packing is particulate in nature. At the other end of the tube a fitting such as illustrated in FIG. 5 or FIG. 2 will be provided so that the frit 36 prevents the loss of the particulate medium, but allows the liquid carrier to pass therethrough. When the column has been packed, and the packing is arranged so as to be flush with the end of the tube 32 as shown in FIGS. 2, 3 and 5, the other end fitting with its frit is applied. The packing is then tested by a known technique. The end fittings are then provided with blank closure plugs 96 as shown in FIG. 6, which are similar to plugs 90 except that no bore for receiving the pipe work 16 or 18 is provided, and these plugs remain with the column until it is ready for use. Columns in this condition may be stored and transported. In the trade in chromatography columns, the columns may be sold packed and ready for use, or they may be sold empty. Additionally, certain companies may manufacture the tube 32 and the pipe work 16 or 18, whilst 40 in the case of FIG. 2 or 74, 76 of FIG. 5 in the case of FIG. 4.

Figure 8A:
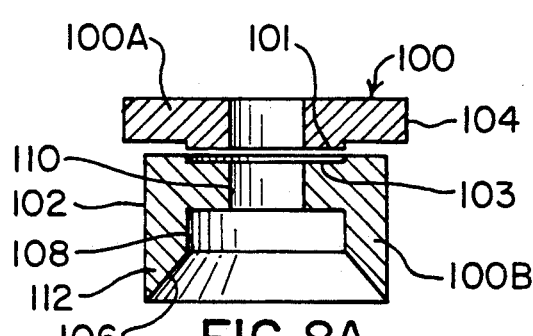
FIG. 8A is a sectional side view of an insert similar to that shown in FIG. 8, but whereas the insert is in two parts.
Figure 7:
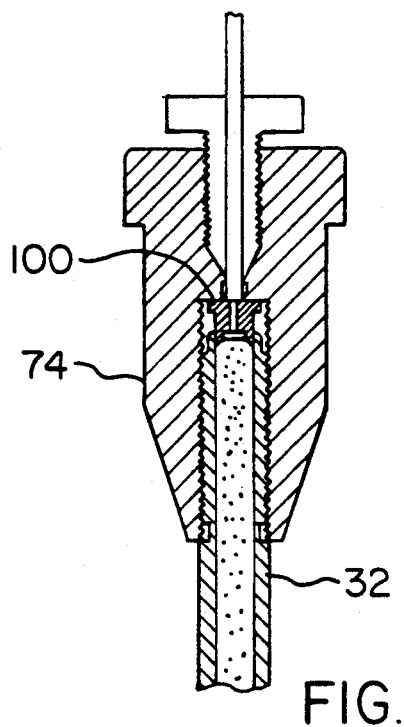
FIG. 7 is a view similar to FIG. 5 but showing a modified arrangement.
Figure 8:
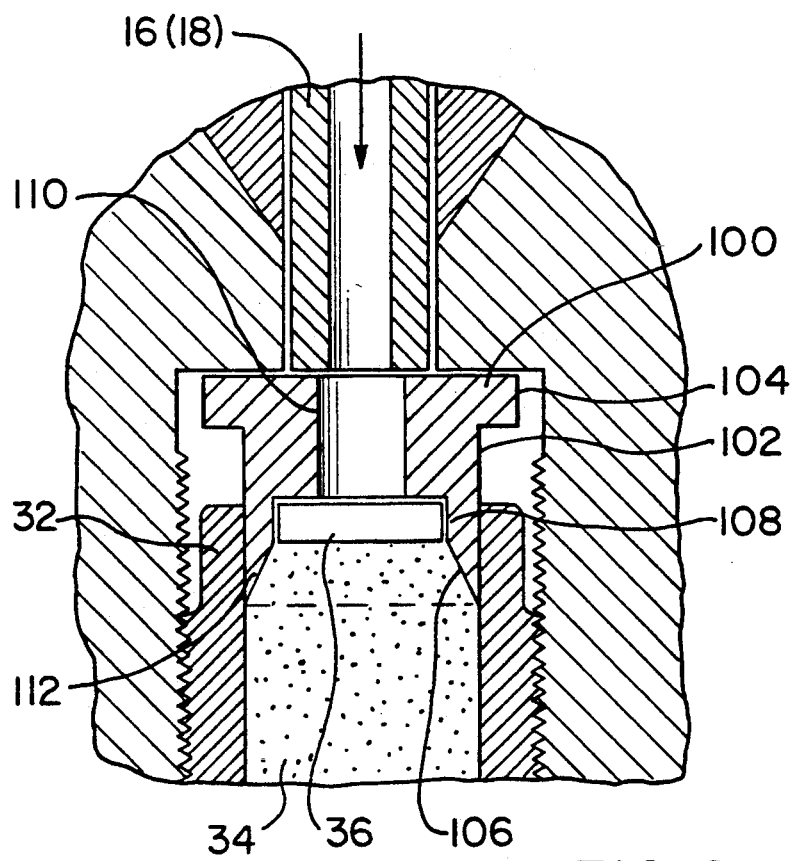
FIG. 8 is a further enlarged view of the detail of the arrangement shown in FIG. 7.

In another embodiment of the invention shown in FIG. 7, the fitting cap 74 is similar to that shown in FIG. 5, but in addition there is provided an insert 100 which fits into the top end of the tube 32, the arrangement being shown in enlarged detail in FIG. 8. Referring to that figure, the insert 100 is shown to comprise a cylindrical plug 102 provided with an upper flange 104 of greater diameter.

The insert 100 has an internal passage defined from the bottom upwards by a frusto conical portion 106 of a cone angle in the range from a few degrees up to almost 90°, but preferably in the region of 30°, a cylindrical portion 108 which receives the frit 36, and a connecting smaller diameter bore 110 which couples with the end of the pipe work 16 or 18. The bore 110 is in fact of a greater diameter than the internal diameter of the pipe work 16 or 18 so that there is in fact created a ferrule depth between the end of the pipe work 16 or 18 and the frit 36.

Because of the frusto conical bore 106, the lower end of the insert 100 in fact forms a flared skirt, and as the insert is pushed into the top of the adsorbent medium 34 either by the screwing on of the fitting 74 and/or by virtue of the flow through the column of the mixture, the column internal pressure which is applied on the skirt portion 112 forces it outwardly into sealing engagement with the inner surface of the tube 32, and excellent sealing results.

A further advantage of the insert is that should the medium 34 develop voids as a result of settling following the packing and use thereof, the plug or cap 74 can be adjusted by screwing so that the insert can be forced into the tube 32 in order to compensate for this void and thereby reduce dead volume. Such voids heretofore had to be elliminated by repacking or by "topping off" the column. It should be mentioned that with use, a chromatography column may lose efficiency such that on the elution curve graphs there may appear shoulders and double peaks which may result from voids inside the adsorbent medium which arise because of dispersion of the sample components in the solvent in the dead spaces in the form of channels or voids, and because of the multiple flow paths through the column caused by the flow characteristics of these dead spaces. The said insert helps reduce these dead spaces in that it can be forced into the column tube compacting the medium 34.

Forming the insert in a plastics material as referred to herein presents further advantages insofar as the skirt portion 112 of the insert will have a degree of flexibility and that flexibility will be particularly useful in that the skirt will be flared outwardly into good sealing contact with the inner surface of the tube 32 when the insert is forced into the column or during operation when the column is internally pressurised. The insert forms in effect an adjustable self sealing component.

FIG. 8 shows a one piece insert, preferably made in plastics material. FIG. 8A shows that the same insert may be made in two pieces, namely a sleeve piece 100A and a ring piece 100B which fit together by a shoulder and recess arrangement 101, 103. When the pieces 100A, 100B are fitted together, the insert performs in exactly the same manner as the insert of FIG. 8, and reference numerals already used for the description of FIG. 8 have been added to FIG. 8A to designate parts already described in relation to FIG. 8, and no further description is here given.

The advantage of forming the insert in two parts is that one part 100A may be of steel and may be recoverable and reuseable even if the other part 100B which preferably is in plastics, is not.

Figure 9A:
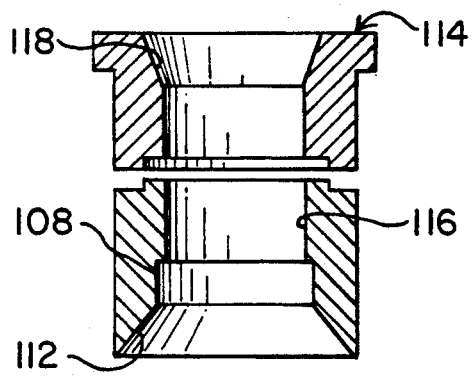
FIG. 9A is a sectional side view of an insert similar to that shown in FIG. 9, but wherein the insert is in two parts.

As mentioned herein before, the insert of FIGS. 8 and 8A does have a ferrule depth, but this can be eliminated if the insert is appropriately modified as illustrated in FIGS. 9 and 9A. In this figure the insert which is indicated by reference 114 has the same skirt portion 112, bore 108 for receiving the frit 36, but the central bore section 110 is replaced with a bore section of larger diameter and indicated by reference 116 whilst the top of the passageway through the insert is frusto conical as indicated by reference 118 to receive the ferrule shaped end 94 of the ferrule clamping plug 92. The pipe work 16 or 18 now extends through the insert and into face to face contact with the frit 36.

It will be understood that when the end fitting 74 is being screwed to the tube 32, the shoulder 115 of the fitting 74 thrusts upon the top surface (thrust surface) 117 of the insert 114 and the insert 114 is forced into the top of the tube as shown forming a compact face to face contact with the adsorbent medium 34, and to anchor the pipe work 16 or 18 to the fitting 74, the plug 92 is simply screwed into the fitting 74, so that the ferrule shaped end 94 wedges against the pipe work 16 or 18 and locks thereto by virtue of the wedging action of the bore section 118.

FIG. 9A shows how the insert of FIG. 9 may, similar to FIG. 8A, be made in two parts. Any insert may be made in multiple parts as desired.

The insert 100 of FIG. 8 (8A) and 114 of FIG. 9 (9A) may be appropriately dimensioned to enable the fittings according to the invention to be connected to the column tubes 32 of different manufacturers.

Furthermore, by providing the insert with the flared skirts as shown, effective compaction and engagement of the top end of the packing of absorbant medium takes place, and the resulting column has good sampling injection qualities, particularly when the ferrule depth is eliminated by bringing the pipe work 16 or 18 directly into contact with the column frit.

It will be appreciated that the fitting arrangement described may be provided at each end of the column tube 32 or any of the illustrated and described fittings may be provided at any end of the column tube. Any fitting as described herein may be provided with an insert of which examples are shown in FIGS. 7, 8, 8A, 9 and 9A.

Figure 10:
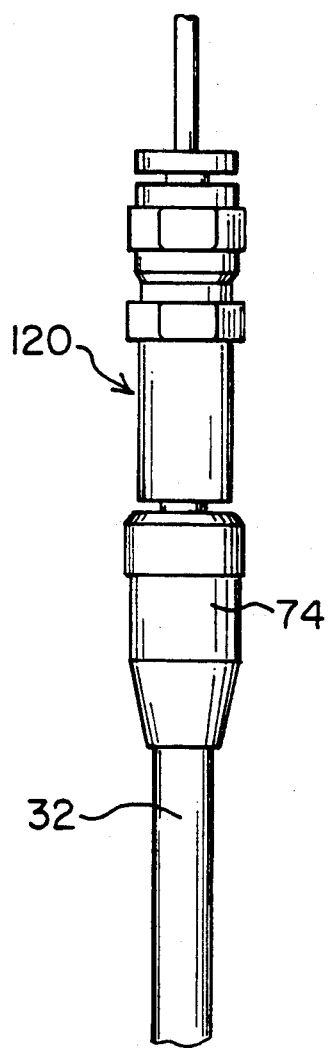
FIG. 10 is a view similar to FIG. 4, but showing only one end of the chromatography column and when provided with a housing for a guard column.
Figure 11:
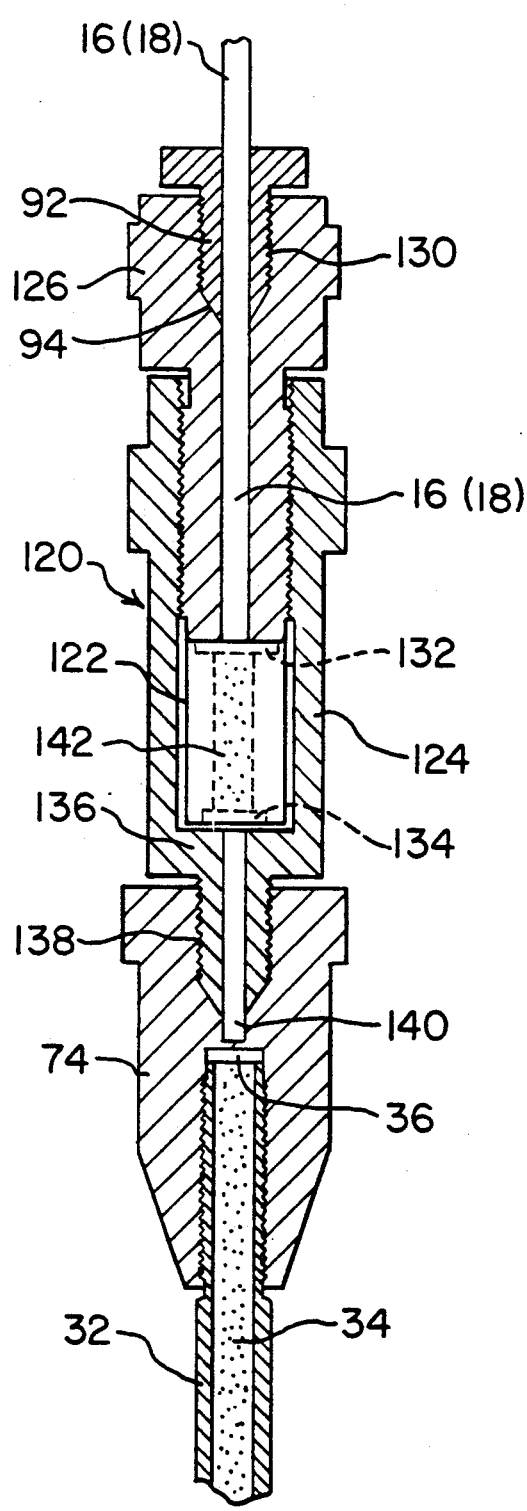
FIG. 11 is a sectional view of the arrangement shown in FIG. 10, but to an enlarged scale.

FIGS. 10 and 11 show a modified form of the invention in which there is attached to the fitting cap 74 at one end of the column tube 32 a holder unit 120 for a guard column 122 (FIG. 11).

As shown in detail in FIG. 11, the holder 120 comprises a sleeve 124 which has a threaded bore and is open at the top end to receive a threaded plug 126. The plug 126 has a bore 128 which receives the pipe work 16 or 18, and at the top end the bore 128 is enlarged and threaded as indicated at 130 and receives a ferrule nut 92 identical to the nut as shown for example in FIG. 5 so that by tightening nut 92 into the bore section 130, the ferrule end 94 will frictionally engage and grip the pipe work 16 or 18 to lock same to the plug 126.

The guard column 122 is provided with frits 132 and 134 at the respective ends, and the pipe work 16 or 18 abuts the top frit 132 whereby ferrule depth is eliminated with the same advantages as described herein.

When the plug 126 is screwed into the sleeve 124, the guard column becomes trapped and locked between the inner end of the plug 126 and the base of the sleeve 124 which is closed by section 136. The said base 136 is provided with an integral ferrule plug extension 138 which is screw threaded into the cap 74 similar to plug 92, so as to frictionally grip a length of pipe work 140 (which is similar to pipe work 16 or 18) to the plug extension 138. The pipe work 140 seats against the frit 134 in the guard column 122, and also against the frit 36 at the top of the column tube 32.

The guard column 122 is to pretreat the sample before it passes through the adsorbent medium 34, in order to remove impurities so preventing the adsorbent medium at the top of the column from becoming contaminated, which may render the whole column unusable, which represents a wastage of a relatively large amount of uncontaminated adsorbent medium. The guard column 122 is a short tube of inner bore diameter which is the same as the inner diameter of the tube 32, and it contains an appropriate adsorbent medium 142. The use of guard columns in chromatography is well known, but the arrangement disclosed in FIGS. 10 and 11 comprises a specific construction providing particular advantages in that the holder 120 is provided with ferrule extension screw 138, and plug 126 is provided with a bore 128 to receive the pipe work 16 or 18 and is also adapted to receive a ferrule plug 92.

As with the previous embodiments described herein, the various components preferably are in the said plastics material. Additionally the arrangement of FIGS. 10 and 11 can be provided with inserts for example as described in relation to FIGS. 7, 8, 8A, 9 and 9A.

Where a ferrule seat and ferrule end of conical form are provided, the cone angle may be any suitable, but it is preferred that the cone angle be 15° to 45°, and preferably 30°.

The invention has particular advantages in the aspect of utilisation of the inserts, especially inserts wholly or partly of plastics material, and of the general configuration set forth herein, as such inserts effectively are void compensaters in that they can be moved into the column tube to eliminate voids being dead spaces or dead volumes, whereby the operation of the column is enhanced.

I claim:

1. A single piece insert for use with a chromatography column comprising a hollow column tube holding packing medium through which fluent material is received from pipework and passed therethrough, said column tube having at least one threaded open end, and adapted to have adjustable threaded external end fittings connected thereto, wherein the improvement consists of: a single piece insert adapted to be slidably inserted in at least one of said column open ends and surrounded by said end fittings, said insert consisting of:
   a) a single piece body portion which is adapted to slidably extend into an open end of a column tube and seal the tube, whether said body portion is partially or fully inserted in the tube;
   b) a passage through said insert to enable the passage through said insert of fluent material to be passed through the column; and
   c) thrust face means integrally connected to said body portion for engagement with a threaded end fitting; whereby adjustment of the end fitting effects adjustment of the extent to which said body portion of said insert slidably projects into the column tube.

2. The improvement of the single piece insert, according to claim 1, wherein said body portion has an end adapted to locate inside the column tube, said end being a skirt of tapering thickness which is adapted to deflect into sealing engagement with the inside of the column tube, whether said body portion is partially or fully inserted into the tube.

3. The improvement of the single piece insert, according to claim 2, wherein said insert is in two pieces, in which said thrust face means is metal and in which said body portion is of plastic.

4. The improvement of the single piece insert, according to claim 1, wherein said insert has a first end which is adapted for location either partially or fully in the column tube and a second opposed end whereat said thrust face means is located, and said passage is axial from said first end to said second end:
   a) a frusto conical portion within said passage and which tapers inwardly from said first end;
   b) a column frit within said passage;
   c) a shouldered portion within said passage which receives said column frit; and also
   d) a remainder portion within said passage which extends from said shouldered portion to said second end.

5. The improvement of the single piece insert, according to claim 4, wherein said passage remainder portion comprises a portion for receiving pipe work by which fluent material is supplied to the column, and a conical ferrule seat portion.

6. The improvement of the single piece insert, according to claim 4 or 5, wherein said insert has a flange adjacent said body portion for limiting the extent to which said insert extends into a column tube.

7. The improvement of the single piece insert, according to claim 4 or 5, wherein said insert is formed in one piece of synthetic plastic material.

8. The improvement of the single piece insert, according to claim 1, wherein said insert has a flange adjacent said body portion for limiting the extent to which said insert extends into a column tube.

9. The improvement of the single piece insert, according to claim 8, wherein said insert is of circular axial cross section and of T-shaped radial cross section.

10. The improvement of the single piece insert, according to claim 1, wherein said insert is formed in one piece of synthetic plastic material.

11. A chromatography column comprising: a hollow tube holding packing medium through which fluent material is received, and having a pair of opposed open ends, at least one of which ends includes a
portion which is externally threaded; adjustable internally threaded external end fittings connected to at least one open end of said column tube and including:
a single piece slidable insert embodied in at least one of said end fittings, said insert consisting of:
a) a body portion which is adapted to extend into an open end of the column tube and press against the packing medium therein, and sealingly engage the inner surface of said column tube whether said body portion is partially or fully inserted into said tube; and
b) a passage through said slidable insert to enable the passage through said insert of the fluent material to be passed through the column; the adjustable end fitting being adjustable to adjust the extent to which said insert projects into the column tube.

12. The column according to claim 11, wherein said body portion of said slidable insert has an end inside the column tube, said end being a skirt of tapering thickness which is adapted to deflect into sealing engagement with the inside of the column tube.

13. The column according to claim 11, wherein said slidable insert has a first end which locates in the column tube and a second end having a thrust face means engaged by said adjustable end fitting; said adjustable end fitting including a threaded internal portion, so that it is adjustable by screwing to said threaded external portion of said tube end to adjust the extent to which said slidable insert enter the column tube.

14. The column according to claim 13, wherein the insert is in two pieces, one of which is of metal and comprises said thrust means, and the other of which, which includes the body portion, is of plastic.

15. A single piece insert for use with a chromatography column comprising a hollow column tube holding packing medium through which fluent material is passed, wherein a hollow column tube has an inner surface and an external surface and a pair of opposed open ends, at least one of which open ends is externally threaded; and at least one adjustable external end cap having a first end, a second end, and an axial passage therethrough from its first end to its second end, wherein the first end is hollow and is internally threaded for screwing connection to an externally threaded open end of the column tube, and a second end remote from its first end, the second end having an inner end surface, wherein the improvement comprises:
a single piece insert, said insert consisting of in combination as a single integrated piece, a body portion having a substantially continuous outer surface, a first end, a second end, and a passage through said insert from said first end to said second end to enable the passage through said insert of fluent material, said first end of said insert being adapted to slidably extend into an open end of the hollow column tube in a manner such that said first end is caused to press against adjacent packing medium within that hollow column tube, while said outer surface of said body portion of said insert is adapted to sealingly engage the inner surface of that hollow column tube whether said body portion is partially or fully inserted into that hollow column tube, said second end of said insert having thrust face means, said insert being adapted to be enclosed within the first hollow end of an adjustable external end cap in screwing connection to an externally threaded open end of that hollow column tube in a manner such that said thrust face means of said second end of said insert is driven by the inner end surface of the adjustable end cap; whereby when said single piece insert is inserted into an open externally threaded end of the hollow column tube and an internally threaded end cap is connected to that hollow column tube around said insert by screwing the end cap to the threaded external end portion of that hollow column tube, the end cap adjusts the extent to which said insert projects into the hollow column tube to press against and pack adjacent packing medium within the hollow column.

16. A chromatography column comprising:
a hollow column tube holding packing medium through which fluent material is received, said hollow column tube having an inner surface and an external surface and a pair of opposed open ends, at least one of which said open ends is externally threaded;
at least one adjustable external end cap, each said end cap having a first hollow end which is internally threaded and in screwing connection to one of said externally threaded open ends of said column tube, and a second end remote from said first end, said second end having an inner end surface and an external end surface, said end cap having an internally threaded axial passage therethrough from said first end to said second end; and
at least one single piece insert, said insert being located within one externally threaded open end of said column tube, said insert consisting of a single integrated piece, a body portion having an outer surface and a first end and a second end, and a passage through said insert from said first end to said second end to enable the passage through said insert of the fluent material to be passed through the column; said first end of said insert being adapted to extend into an open end of said column tube in a manner such that said first end presses against adjacent packing medium within said column while said outer surface of said insert sealingly engages said inner surface of said column tube, whether said body portion is partially or fully inserted into said column tube, said second end of said insert having a thrust face means, said insert being adapted to be enclosed within said first hollow end of one of said adjustable external end caps in such a manner that said thrust face means of said second end of said insert is engaged by said inner end surface of said second end of said adjustable end cap; whereby when said single piece insert is inserted into an open externally threaded end of said column tube and an internally threaded end cap is connected to said column tube around said insert by screwing said end cap to said threaded external end portion of said column tube, said end cap adjusts the extent to which said insert projects into said column tube to press against and pack adjacent packing medium within the column.

17. The chromatography column of claim 16 wherein said external end surface of said second end of said adjustable external end cap is in the form of a seat, and said axial passage at said second end is internally threaded for receiving a clamping nut.

18. The column according to claim 17, wherein said external end cap has an outer profile comprising from the first end to the second end, a first frusto conical portion, a cylindrical portion and a ring having knurling or flats to facilitate turning of the end cap.

19. The column according to claim 17, wherein the said passage in said insert comprises from said first end to the second end;
a) an internal frusto conical portion;
b) a column frit;
c) a shouldered portion within said passage which receives said column frit; and
d) a remainder portion within said passage which extends from the shouldered portion to said second end.

20. The column according to claim 17, including a frit at one end of the column tube contacting the packing medium and pipe work connected to said external end cap for the supply of fluent material to the column, said pipe work having an end located in said internally threaded axial passage at said second end of said external end cap, and butting the frit, and further including a clamping screw having a ferrule end threaded into said internally threaded axial passage clamping the pipework to the end cap.

21. The column according to claim 17, including an attachment to the internally threaded axial passage at said second end of said external end cap, said attachment embodying a holder holding a guard column, wherein said holder comprises an internally threaded holder cup, an externally threaded holder plug which is screwed into said holder cup and traps the guard column between the end of the holder plug and the base of the holder cup, each of said holder plug and holder cup having a passage therethrough for the passage of the fluent material through the holder and guard column, said cup comprising a ferrule screw extension which screws into said internally threaded axial passage at said second end of said external end cap and the said passage of the holder plug having a threaded portion for receipt of a female screw.

22. The column according to claim 21, including a frit at the top end of the guard column and pipework connected to said holder plug for the supply of fluent material to the guard column, said pipework having an end located in said holder plug passage and butting said frit, and further including a clamping screw having a ferrule end threaded into said threaded portion of the holder plug passage clamping the pipework to the external end cap.

23. The column according to claim 21, including a length of pipework in said holder cup and extending through said ferrule screw extension, a frit at the lower end of the guard column and a frit at one end of the column tube, said length of pipework having ends respectively butting the said frit at the lower end of the guard column and at the one end of the column tube.

* * * * *